United States Patent [19]

Laure

[11] 4,134,157
[45] Jan. 16, 1979

[54] INSERTION TOOLS
[75] Inventor: George R. Laure, Kalamazoo, Mich.
[73] Assignee: Laure Prosthetics, Inc., Portage, Mich.
[21] Appl. No.: 821,545
[22] Filed: Aug. 3, 1977
[51] Int. Cl.² .................... A61F 1/24; A61B 17/00
[52] U.S. Cl. ........................... 3/1.91; 128/303 R; 128/92 EC
[58] Field of Search .................. 3/1.9–1.911; 128/92 C, 303 R, 92 E, 92 EC

[56] References Cited
U.S. PATENT DOCUMENTS

| 3,857,389 | 12/1974 | Amstutz | 128/92 EC |
| 3,990,118 | 11/1976 | Strickland et al. | 3/1.91 |
| 4,011,603 | 3/1977 | Steffee | 3/1.91 |

*Primary Examiner*—Ronald L. Frinks

*Attorney, Agent, or Firm*—Blanchard, Flynn, Thiel, Boutell & Tanis

[57] ABSTRACT

Tool for inserting a component of a prosthetic implant, primarily a component of a finger knuckle joint, said component having a joint portion and a prong portion. There is provided a tool having at one end thereof a suitable receptacle for receiving said joint portion and holding same firmly for inserting the prong portion of said implant as desired into a bone and then easily detaching said tool from the prosthesis. In the disclosed embodiment, the prosthesis has in its joint portion a somewhat cylindrical bearing part and the tool for handling same is provided with a generally cylindrical receptacle for receiving same with, however, one portion thereof cut out for the easy removal of the tool from said prosthesis.

5 Claims, 8 Drawing Figures

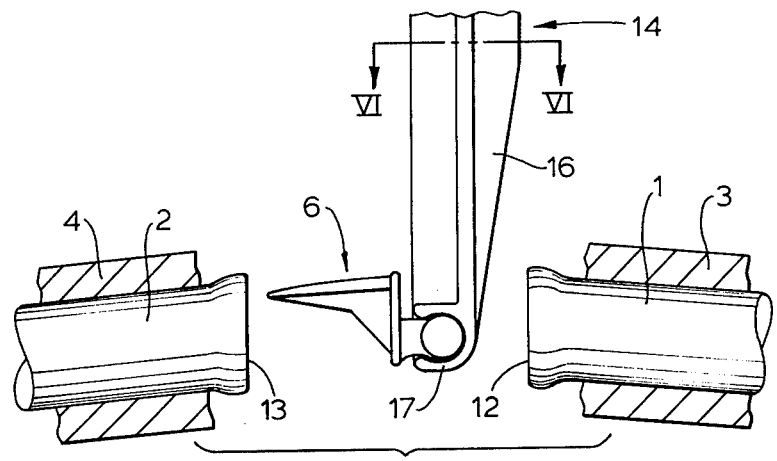
FIG. 1
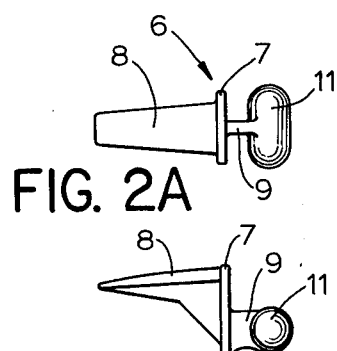
FIG. 2A
FIG. 2B
FIG. 2C
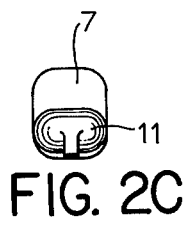
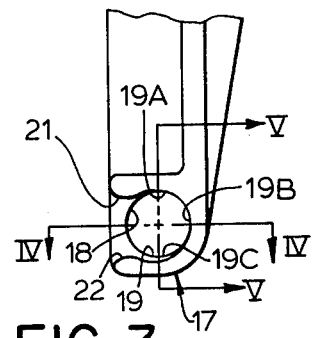
FIG. 3
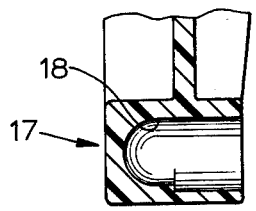
FIG. 5
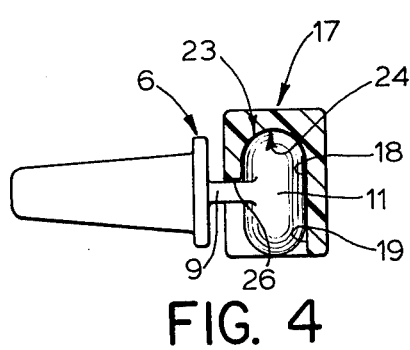
FIG. 4
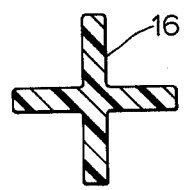
FIG. 6

INSERTION TOOLS

FIELD OF THE INVENTION

The invention relates to a surgical tool and particularly to such a tool adapted for receiving a finger joint prosthesis having a joint portion and a prong portion and holding same firmly for manipulation as required while and for the purpose of inserting said prong portion into a suitable opening in the bone to which such prosthesis is being applied.

BACKGROUND OF THE INVENTION

The provision of prostheses for various types of joints in the human body and particularly for finger joints is not a new art but it is one in which the level of interest has increased greatly in the last few years. A very large number of such prostheses have been designed and offered to the medical profession and thousands thereof have been utilized for replacing patients' joints.

Throughout this work, however, there has been insofar as I am aware, a constant unsolved problem of providing means by which said prostheses could be held, firmly manipulated but easily released during an implant procedure. When it is remembered that many such prostheses, particularly those going into the small joints of a finger are often not more than 1 to 1½ inches long so that each component thereof is approximately ⅝-¾ inch long, that each half must be separately manipulated to position same into the appropriate bone adjacent such joint, that the working space between the adjacent ends of the bones is seldom more than ½-¾ inch, and that the fingers of the acting surgeon are usually at least ½ inch wide, it will be recognized that it is an extremely difficult procedure for the surgeon to hold a component of such prosthesis in his fingers, appropriately insert same into the space between the adjacent ends of the bone and then push the prosthesis into a hole drilled into the bone. The surgeon's fingers in the small space between the bone ends are often simply so large as to obscure the surgeon's view of the working zone, particularly his view of the end of the bone into which the prosthesis is to be inserted, and a great deal of difficulty and inconvenience has thereby been generated.

The problem has been well recognized for a considerable period of time but insofar as I am aware, no solution has been offered therefor.

Accordingly, the objects of the present invention include:

1. To provide a relatively simple tool which will conveniently receive a portion of a prosthesis for a finger joint implant, control same for appropriate insertion thereof into the necessary bone and then be capable of ready removal from the implant by a sufficiently easy motion as not to disturb the position of the implant in the bone.

2. To provide a tool, as aforesaid, which will have no moving parts.

3. To provide a tool, as aforesaid, which can be readily molded from plastics material.

4. To provide a tool, as aforesaid, which will be of sufficient structural simplicity that its mode of operation will be obvious.

Other objects and purposes of the invention will become apparent to persons skilled in this art upon reading the following specification and inspection of the accompanying drawings.

BRIEF DESCRIPTION OF THE DRAWINGS

In the drawings:

FIG. 1 is a somewhat schematicized view of the tool of the invention in the process of inserting the prong portion of an implant into an adjacent bone.

FIGS. 2A, 2B and 2C are top, side and end views, respectively, of one typical finger joint implant with which the specific tool of the invention has been designed for use.

FIG. 3 is a fragmentary side elevational view of a tool embodying the invention.

FIG. 4 is a section taken on the line IV—IV of FIG. 3.

FIG. 5 is a section taken on the line V—V of FIG. 3.

FIG. 6 is a section taken on the line VI—VI of FIG. 1.

DETAILED DESCRIPTION

Referring first to the environment in which said tool is to be used, attention is called to FIG. 1 in which there is shown, somewhat schematically, a pair of adjacent finger bones from which the natural joint has been removed preparatory to implanting the prosthesis. Thus, the bones are indicated at 1 and 2 with the surrounding muscles and skin generally indicated at 3 and 4. A suitable opening, not shown, has been drilled in the facing ends of each of the bones 1 and 2 for the reception of the prong portion of the implant and the cementing of same therein in a conventional manner.

The implant may be of the type shown in U.S. Pat. No. 4,011,603 issued Mar. 15, 1977, to Arthur D. Steffee. For convenient reference here, the portion of the implant with which the particular tool here dealt with is illustrated in FIGS. 2A, 2B and 2C. In such figures, there is shown an implant 6 having a body portion 7 carrying on one side thereof a prong 8 for inserting into the bone and on the other side thereof a neck 9 which carries a somewhat cylindrical head 11. In this embodiment, said head 11 is provided with rounded ends, the overall length of the implant portion 6 is usually about ¾ inch and in a typical surgical proceeding is placed between the ends 12 and 13 of the bones 1 and 2, respectively, which ends can seldom typically be placed more than about 1 to 1¼ inches apart.

Turning now to the tool comprising the invention, same is indicated generally at 14 and comprises a handle 16 and head 17. Said handle is of any desired length, often approximately 5 inches, and may be of any desired cross-sectional shape, here the cross-shape indicated in FIG. 6. At the end of said handle, there is provided the head 17 which is internally contoured to receive the head 11 of the implant in a manner for firm holding thereof. Referring now to FIGS. 3, 4 and 5, it will be seen that approximately one-half of said tool head 17 is provided with an internal opening 18 which is of such size and shape as to receive an end and about one-half of the implant head 11 snugly therein. It is not, however, so tight as to resist either insertion or removal of said implant head thereinto or therefrom.

The other half of said tool head 17 has therein a generally U-shaped opening 19 wherein at least a portion thereof comprises continuations of the corresponding parts of the opening 18. Here, such continuing portions are the upper part 19A and the rearward part 19B of said U-shaped opening 19. The lower part 19C of said U-shaped opening is an approximate continuation of the corresponding part of opening 18 but same is relieved slightly as shown with respect to said corresponding part of the opening 18.

Desirably as appearing in the drawings, but not necessarily, there is also provided lip portions 21 and 22 at the ends of each arm of the walls of said U-shaped opening to provide some assistance in the retention of the implant head 11 therewithin and the walls define an opening greater than 180°.

OPERATION

The use of the tool above described will be self-evident to those skilled in the art but will nevertheless be described to insure a complete understanding of the invention.

As shown in FIG. 4, one end of the head 11 of the prosthesis is inserted into the opening 18 of the tool by moving same axially of said opening 18 from the end thereof defined by the U-shaped opening 19. As shown in FIG. 4, when the end 23 of the prosthesis strikes the end 24 of the opening 18, the neck 9 of the prosthesis will be in contact with, or at least close to, the surface 26 of the tool. Thus, the prosthesis is inserted into the tool by a simple lateral lineal motion between the prosthesis and the tool and no moving parts are required for the tool at all.

With the prosthesis so gripped, same is free for manipulation as required and particularly a wide surface comprising the portion 19B of the U-shaped opening 19 and the adjacent portion of the opening 18 are available for urging of the implant firmly into the bone.

With the implant properly in place, the tool may then be detached from the implant head 11 by a reverse lateral lineal motion between the implant and the tool and no snapping or other application of excessive force is required.

The implant is under complete control of the surgeon at all times by the use of the tool of the invention and yet the portion thereof into which the implant head 11 is received is sufficiently small that it can easily be placed as required between the adjacent ends of the finger bones and the implant and finger bones are fully visible at all times.

While the opening 19 has been indicated above and in the drawings as a generally U-shaped opening with the lips 21 and 22 provided if desired to assist further in the retention of the implant within the toolhead, it will be understood that the extension of said lips 21 and 22 will be determined by the vertical dimension of the neck 9 of the implant. Thus, with an implant whose neck is of narrower vertical dimension than that best shown in FIG. 2B, said lips 21 and 22 may if desired be brought closer together to extend the walls of said opening 19 still further provided only sufficient space is left between said lips to permit passage of the neck 9 therebetween.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. In a tool for inserting a component of a prosthetic implant, said component having a body part with a prong projecting from one side thereof and a neck portion projecting from the other side thereof and a generally cylindrical head at the end of said neck portion, the combination comprising:

a handle with a tool head portion at one end thereof;
said tool head portion having a blind opening in one part thereof dimensioned for snug but slidable reception of the implant head on one side of said neck portion and said tool head portion having a generally U-shaped opening of which the bight portion is generally semicircular and comprising a substantial continuation of the immediately adjacent walls of said blind opening;
whereby when said implant component is in position within said tool, one portion of said implant head will be received snugly in the blind opening of said tool head portion and another portion of said implant head will be against the bight of said U-shaped opening whereby a wall of the blind opening and the wall defining said bight may together be caused to bear against the opposed surface of said implant head.

2. The device of claim 1 wherein the depth of said blind opening is at least as great as the extension of said implant head to one side of said neck portion whereby when said implant head is in position within said tool, said neck portion will lie against a wall adjacent said blind opening.

3. The device of claim 1 wherein said implant head and said blind opening both have generally rounded ends.

4. The device of claim 1 wherein said U-shaped opening is provided with lips on each arm of the walls defining said U whereby said walls define an opening greater than 180°.

5. The device of claim 1 wherein the walls defining said U-shaped opening continue further arcuately to define a generally cylindrical open-ended opening for the snug reception of said implant head with the ends of said walls spaced sufficiently to permit passage of said neck portion therebetween.

* * * * *